(12) United States Patent
Han

(10) Patent No.: US 11,850,049 B2
(45) Date of Patent: Dec. 26, 2023

(54) APPARATUS FOR AUTOMATICALLY MEASURING URINE VOLUME AND SYSTEM FOR AUTOMATICALLY MEASURING URINE VOLUME

(71) Applicant: Sang Ho Han, Seoul (KR)

(72) Inventor: Sang Ho Han, Seoul (KR)

( * ) Notice: Subject to any disclaimer, the term of this patent is extended or adjusted under 35 U.S.C. 154(b) by 446 days.

(21) Appl. No.: 17/130,259

(22) Filed: Dec. 22, 2020

(65) Prior Publication Data

US 2022/0125361 A1  Apr. 28, 2022

(30) Foreign Application Priority Data

Oct. 27, 2020 (KR) .................. 10-2020-0140361

(51) Int. Cl.
*A61B 5/20* (2006.01)
*A61B 10/00* (2006.01)
*A61B 5/145* (2006.01)

(52) U.S. Cl.
CPC .......... *A61B 5/208* (2013.01); *A61B 5/14507* (2013.01); *A61B 10/007* (2013.01)

(58) Field of Classification Search
CPC ... A61B 5/208; A61B 5/14507; A61B 10/007; A61B 5/0002; A61B 5/1459; A61B 5/204; A61B 5/207
See application file for complete search history.

(56) References Cited

U.S. PATENT DOCUMENTS 6,582,379 B1 * 6/2003 Stisen .................... A61B 5/208
                                                      600/580
9,290,296 B2   3/2016 Tom et al.
(Continued)

FOREIGN PATENT DOCUMENTS

| EP | 1795875 B1 | 10/2008 |
|---|---|---|
| KR | 1019990079614 A | 11/1999 |
| KR | 1020000056603 A | 9/2000 |
| KR | 100810075 B1 | 3/2008 |
| KR | 1020110105920 A | 9/2011 |
| KR | 1020140064894 A | 5/2014 |
| KR | 1020180036022 A | 4/2018 |

*Primary Examiner* — Daniel L Cerioni
*Assistant Examiner* — Ari Singh Kane Padda
(74) *Attorney, Agent, or Firm* — Culhane Meadows PLLC; Robert C. Klinger

(57) ABSTRACT

Disclosed are an apparatus for automatically measuring urine volume and a system for automatically measuring urine volume. The apparatus for automatically measuring urine volume of the present disclosure includes a urine container to which a urine catheter is connected, wherein an insertion hole is formed in an upper portion of the urine container, a hollow tube inserted into the insertion hole in a gravity direction, a floating body inserted into the hollow tube so as to move up and down and having buoyancy to float on the urine, and a distance sensor provided at an upper portion of the hollow tube so as to measure a distance to the floating body, wherein the volume of urine in the urine container is measured by using a measurement of the distance sensor. According to the present disclosure, the apparatus for automatically measuring urine volume and the system for automatically measuring urine volume are configured to measure the correct volume of urine automatically and continuously, regardless of the tilt of a urine container, the weight of a Foley catheter, and the presence of a nurse who directly checks the urine volume, so as to accurately recognize a change in the volume of urine and anticipate a probable emergency situation based on the change in the volume of urine.

6 Claims, 9 Drawing Sheets

(56) References Cited

U.S. PATENT DOCUMENTS

2017/0100068 A1\* 4/2017 Kostov ................. A61M 39/28
2021/0069455 A1\* 3/2021 Kuzelka ................ A61M 16/18
2022/0354402 A1\* 11/2022 Hong ....................... A61B 5/20

\* cited by examiner

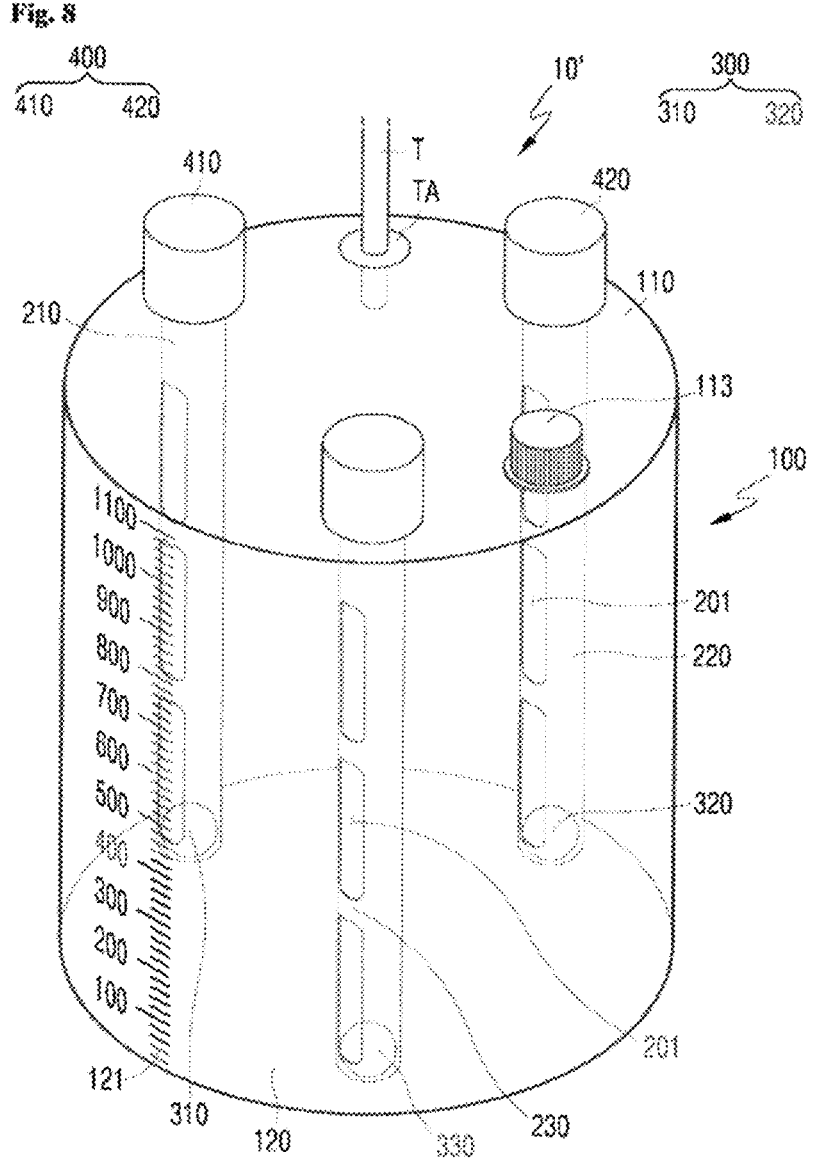

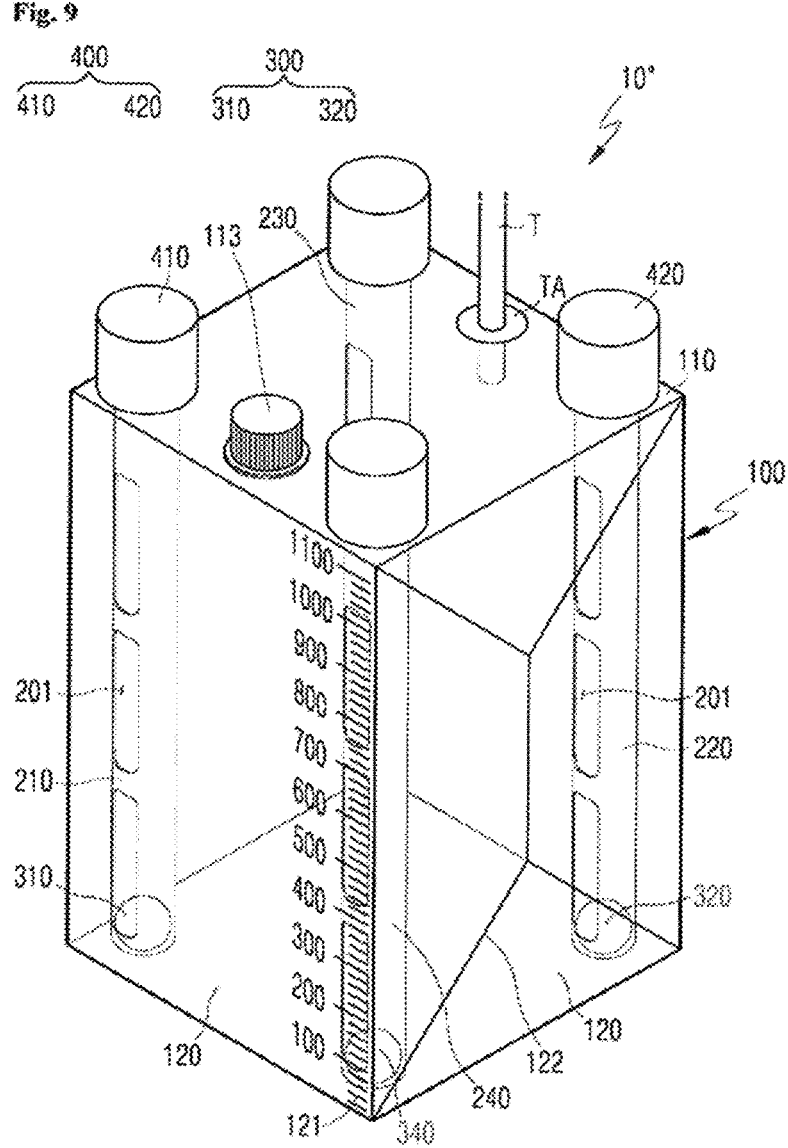

APPARATUS FOR AUTOMATICALLY MEASURING URINE VOLUME AND SYSTEM FOR AUTOMATICALLY MEASURING URINE VOLUME

CROSS-REFERENCE TO RELATED APPLICATION

This present application claims the benefit of priority to Korean Patent Application No. 10-2020-0140361, entitled "AUTOMATIC APPARATUS FOR URINE MEASUREMENT AND AUTOMATIC SYSTEM FOR URINE MEASUREMENT" filed on Oct. 27, 2020, in the Korean Intellectual Property Office, the entire disclosure of which is incorporated herein by reference.

FIELD

The present disclosure relates to an apparatus for automatically measuring urine volume and a system for automatically measuring urine volume and, more particularly, to an apparatus for automatically measuring urine volume and a system for automatically measuring urine volume configured to measure the correct volume of urine continuously and automatically.

BACKGROUND

Maintaining the balance of body fluid is essential to be in good health. Accordingly, it is very important to assess water balance in the body. When it comes to a patient in the intensive care unit, in particular, when the body fluid balance is disturbed, serious complications such as congestive heart failure, pulmonary edema, delirium, and the like may occur, resulting in a fatal condition.

In general, there are three methods to assess body fluid balance. First is a clinical test by which serum, urine osmolality, serum sodium concentration, natriuretic peptide, etc. are tested. Second, there is a subjective observation method in which skin elasticity, thirst, mucous membrane humidity, and the like are observed. The third method is an objective and non-invasive assessment method in which weight, intake and output (I&O), the number of bowel movements, and the like are measured.

In the past, patients had to carry a urine bag, and the urine collected in the urine bag had to be poured into a beaker with graduations marked thereon every hour in order to measure the volume of urine. Recently, urine bags on which volume graduations are printed have been used, and thus the urine in the urine bag does not have to be poured into a beaker every hour.

However, even when the urine bag on which volume graduations are marked is used, the correct volume of urine cannot be measured if the urine bag is tilted. In addition, a nurse has to visit the patient every hour and measure the urine volume by checking the urine bag with the naked eye, which means that the labor of a nurse in charge is continuously and periodically required. Furthermore, when such a urine bag with volume graduations printed thereon is used, an emergency situation cannot be recognized right away based on a change in the amount of urine.

In this regard, Korean Patent Publication Registration No. 810075 (hereinafter referred to as "related art") discloses a monitoring system using a urine mass measuring sensor. The urine mass measuring sensor of the related art includes a container holding member for hanging a urine collecting container for collecting urine excreted from the body of a patient, and a load cell connected with the container holding member for outputting a predetermined electric signal proportional to the weight of urine filled in the urine collecting container connected with the container holding member.

As the load cell of the monitoring system outputs an electric signal corresponding to the weight of urine, the invention of the related art has an advantage in that a medical person in charge can easily check and manage urine mass of patients without having to visit each patient to check the urine collecting container or write a checklist.

However, the concentration of urine changes according to the state of the patient. Thus, the monitoring system of the related art has a deficiency in that it is difficult to accurately convert the weight of the urine into volume.

In addition, in the monitoring system of the related art, the load on the load cell necessarily includes some of the weight of a Foley catheter connected to the urine collecting container. Accordingly, for the load cell not to include the weight of the Foley catheter, the Foley catheter should be installed in such a manner that the weight of the Foley catheter is fully loaded on a load cell supporting member, which is, however, practically difficult.

That is, the monitoring system of the related art still does not overcome the deficiency of being unable to measure the correct volume of urine. Accordingly, the related art still involves the deficiency in which nurses have to visit each patient in order to check the correct volume of urine, and it is difficult to accurately recognize an emergency situation right away based on the change in the volume of urine.

RELATED ART DOCUMENTS

Patent Documents

Korean Patent Publication Registration No. 810075 (Registration date: Feb. 27, 2008)

SUMMARY

An aspect of the present disclosure is directed to providing an apparatus for automatically measuring urine volume and a system for automatically measuring urine volume characterized in that the correct volume of urine is automatically and continuously measured, regardless of the tilt of a urine container, the weight of a Foley catheter, and the presence of a nurse who directly checks the urine volume, so as to accurately recognize a change in the volume of urine and anticipate a probable emergency situation based on the change in the volume of urine.

To this end, the present disclosure provides the apparatus for automatically measuring urine volume, the apparatus including: a urine container to which a urine catheter is connected, wherein an insertion hole is formed in an upper portion of the urine container; a hollow tube inserted into the insertion hole in a gravity direction; a floating body inserted into the hollow tube so as to move up and down and having buoyancy to float on the urine; and a distance sensor provided at an upper portion of the hollow tube so as to measure a distance to the floating body, wherein the volume of urine in the urine container is measured by using a measurement of the distance sensor.

One or more through holes may be formed in the hollow tube such that urine can flow into the hollow tube.

An adhering portion to be attached around the insertion hole may be formed in the upper portion of the hollow tube, and an upper surface of the adhering portion may be attached around a bottom edge of the distance sensor such that the urine container is sealed.

A side surface of the urine container may be configured to be folded and unfolded, and an attachment portion to be attached to an inner bottom surface of the urine container may be formed in a lower portion of the hollow tube. The side surface of the urine container may be maintained in an unfolded state by a rigidity of the hollow tube.

The urine container may be formed in a three-dimensional shape in which a top surface and a bottom surface of the urine container are parallel to each other. The hollow tube may be two or more hollow tubes, and the hollow tubes may include a first hollow tube and a second hollow tube, which may be disposed at symmetrical positions about a center of the top surface of the urine container. The top surface and the bottom surface of the urine container may be maintained to be parallel to each other by the rigidity of the first hollow tube and the second hollow tube.

In addition, the present disclosure also provides the system for automatically measuring urine volume, the system including: the apparatus for automatically measuring urine volume; and an output device configured to receive the measurement of the distance sensor and output the volume of urine.

The urine container may be formed in a three-dimensional shape in which the top surface and the bottom surface of the urine container are parallel to each other. The distance sensor may be two or more distance sensors, and the distance sensors may include a first distance sensor and a second distance sensor. The first distance sensor and the second distance sensor may be provided at symmetrical positions about the center of the top surface of the urine container, such that even when the urine container is tilted, an average of a measurement of the first distance sensor and a measurement of the second distance sensor corresponds to the volume of urine. The output device may calculate the average of the measurements of the first distance sensor and the second distance sensor and output the volume of urine.

According to the present disclosure, the apparatus for automatically measuring urine volume and the system for automatically measuring urine volume are characterized in that as the volume of urine in the urine container is measured by using the measurements of the distance sensors, and the output device outputs the volume of urine, the correct volume of urine may be automatically and continuously measured regardless of the tilt of the urine container, the weight of a Foley catheter, and the presence of a nurse who directly checks the volume of urine, so as to accurately recognize a change in the volume of urine and anticipate a probable emergency situation based on the change in the volume of urine.

BRIEF DESCRIPTION OF THE DRAWINGS

The foregoing and other aspects, features, and advantages of the invention, as well as the following detailed description of the embodiments, will be better understood when read in conjunction with the accompanying drawings. For the purpose of illustrating the present disclosure, there is shown in the drawings an exemplary embodiment, it being understood, however, that the present disclosure is not intended to be limited to the details shown because various modifications and structural changes may be made therein without departing from the spirit of the present disclosure and within the scope and range of equivalents of the claims. The use of the same reference numerals or symbols in different drawings indicates similar or identical items.

FIG. 8 is a perspective view of an apparatus for automatically measuring urine volume according to another embodiment of the present disclosure.

FIG. 9 is a perspective view of an apparatus for automatically measuring urine volume according to yet another embodiment of the present disclosure.

DETAILED DESCRIPTION

Figure 1:
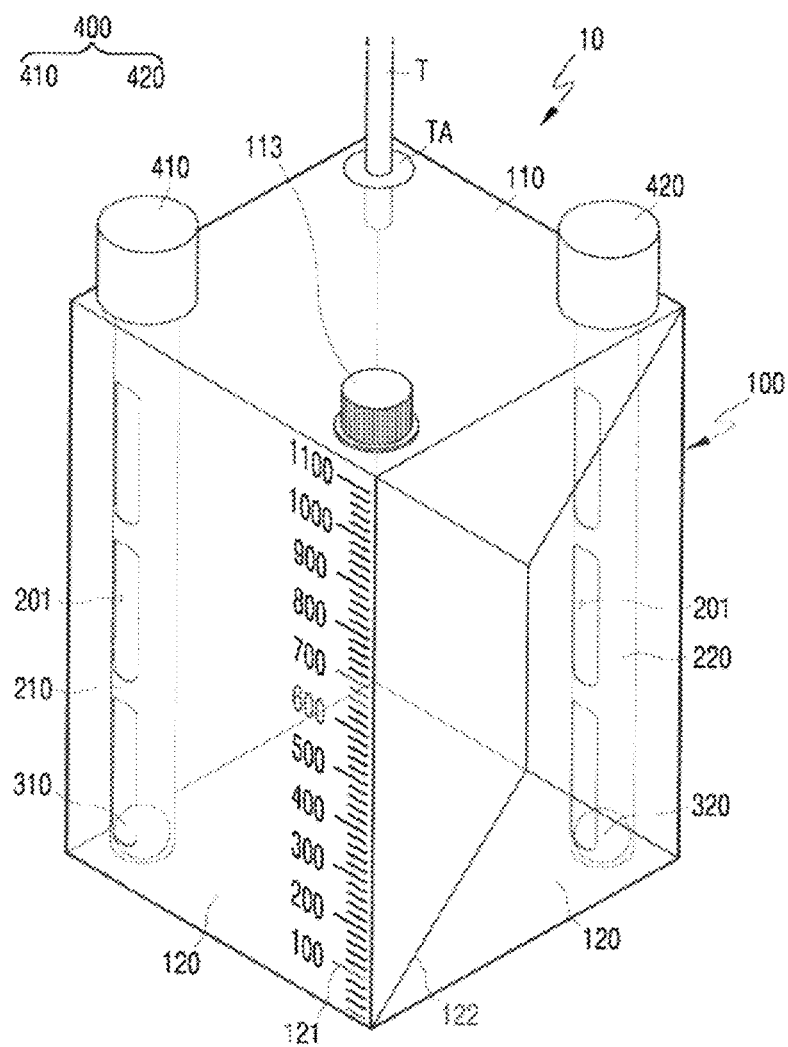
FIG. 1 is a perspective view of an apparatus for automatically measuring urine volume according to an embodiment of the present disclosure.

Advantages and features of the present disclosure and methods for achieving them will become apparent from the descriptions of aspects herein below with reference to the accompanying drawings. However, the present disclosure is not limited to the aspects disclosed herein but may be implemented in various different forms. The aspects are provided to make the description of the present disclosure thorough and to fully convey the scope of the present disclosure to those skilled in the art. It is to be noted that the scope of the present disclosure is defined only by the claims.

The shapes, sizes, ratios, angles, the number of elements given in the drawings are merely exemplary, and thus, the present disclosure is not limited to the illustrated details. Like reference numerals designate like elements throughout the specification.

In relation to describing the present disclosure, when the detailed description of the relevant known technology is determined to unnecessarily obscure the gist of the present disclosure, the detailed description may be omitted.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

The term "or" is meant to be inclusive and means either, any, several, or all of the listed items.

Hereinafter, preferable exemplary embodiments of the present disclosure will be described in detail referring to the attached drawings. In the following description, known functions or features will be omitted in order to clarify the gist of the present disclosure.

An apparatus for automatically measuring urine volume and a system for automatically measuring urine volume of the present disclosure are characterized in that the correct volume of urine is automatically and continuously measured, regardless of the tilt of a urine container, the weight of a Foley catheter, and the presence of a nurse who directly checks the urine volume, so as to accurately recognize a change in the volume of urine and anticipate a probable emergency situation based on the change in the volume of urine.

Figure 2:
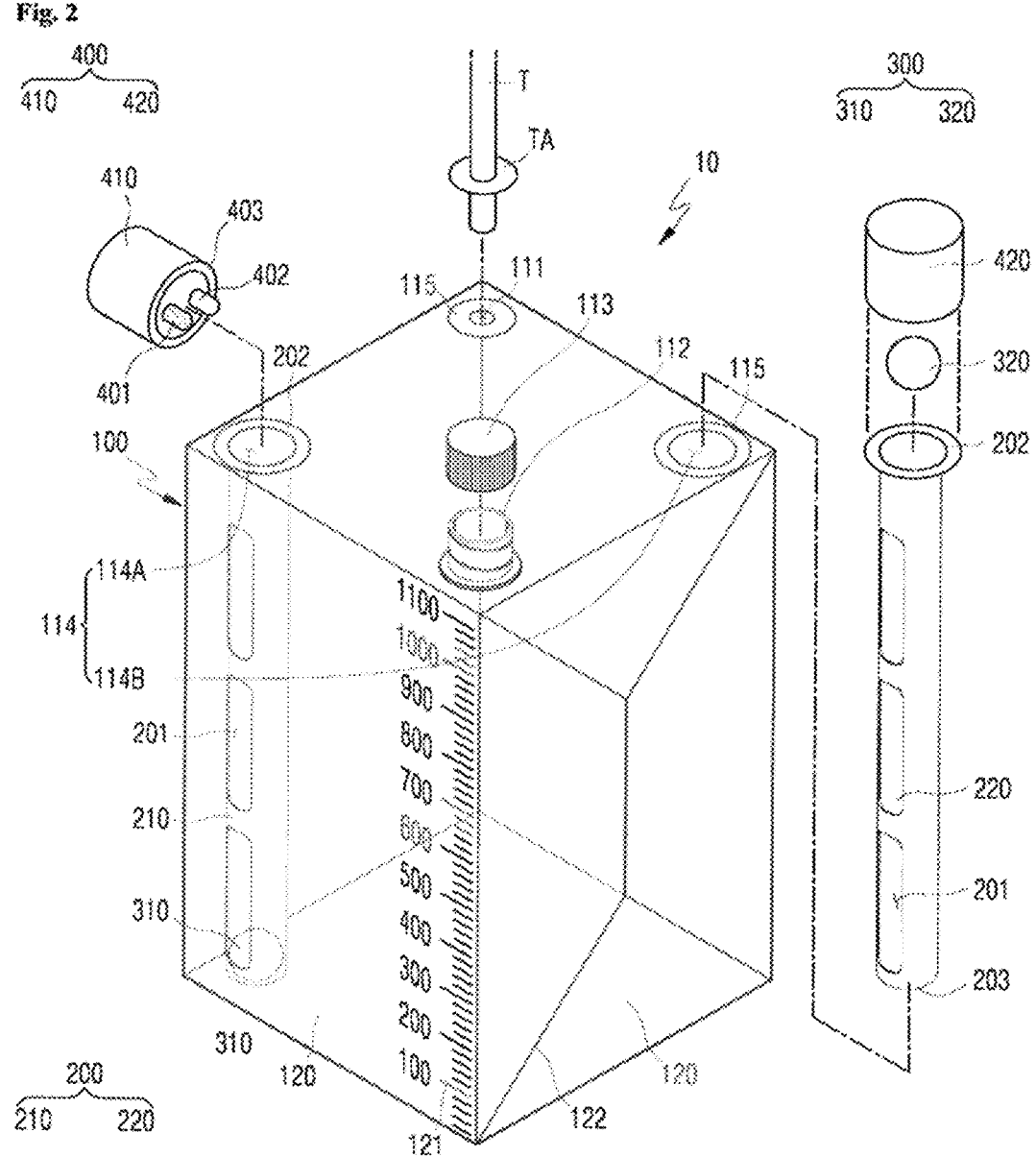
FIG. 2 is an exploded perspective view of the apparatus for automatically measuring urine volume of FIG. 1.

FIG. 1 is a perspective view of an apparatus for automatically measuring urine volume 10 according to an embodiment of the present disclosure. FIG. 2 is an exploded perspective view of the apparatus for automatically measuring urine volume 10 of FIG. 1.

Figure 3:
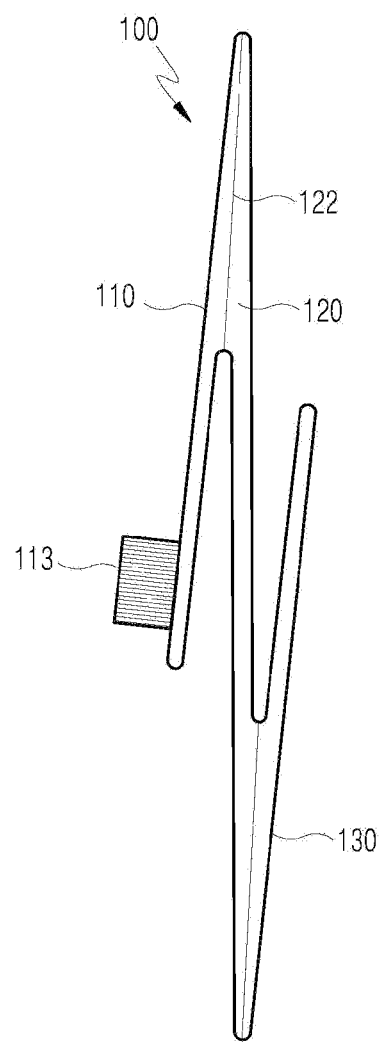
FIG. 3 is a side view illustrating a state in which a urine container of FIG. 1 has been folded.
Figure 4:
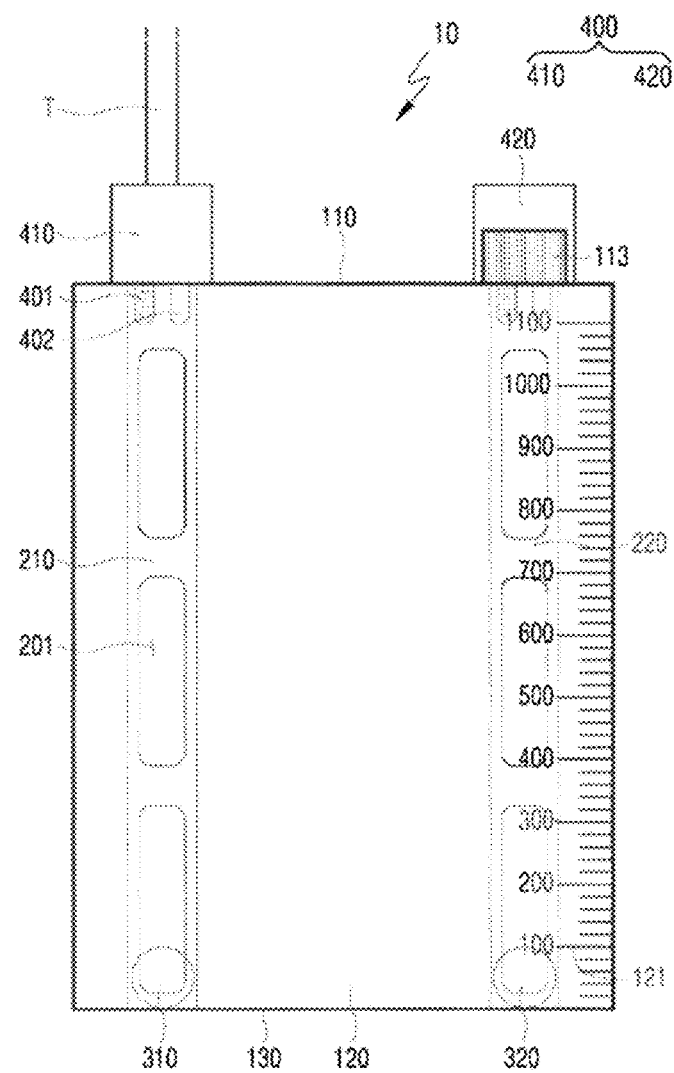
FIG. 4 is a side view of the apparatus for automatically measuring urine volume of FIG. 1.

FIG. 3 is a side view illustrating a state in which a urine container 100 of FIG. 1 has been folded. FIG. 4 is a side view of the apparatus for automatically measuring urine volume 10 of FIG. 1.

Figure 5:
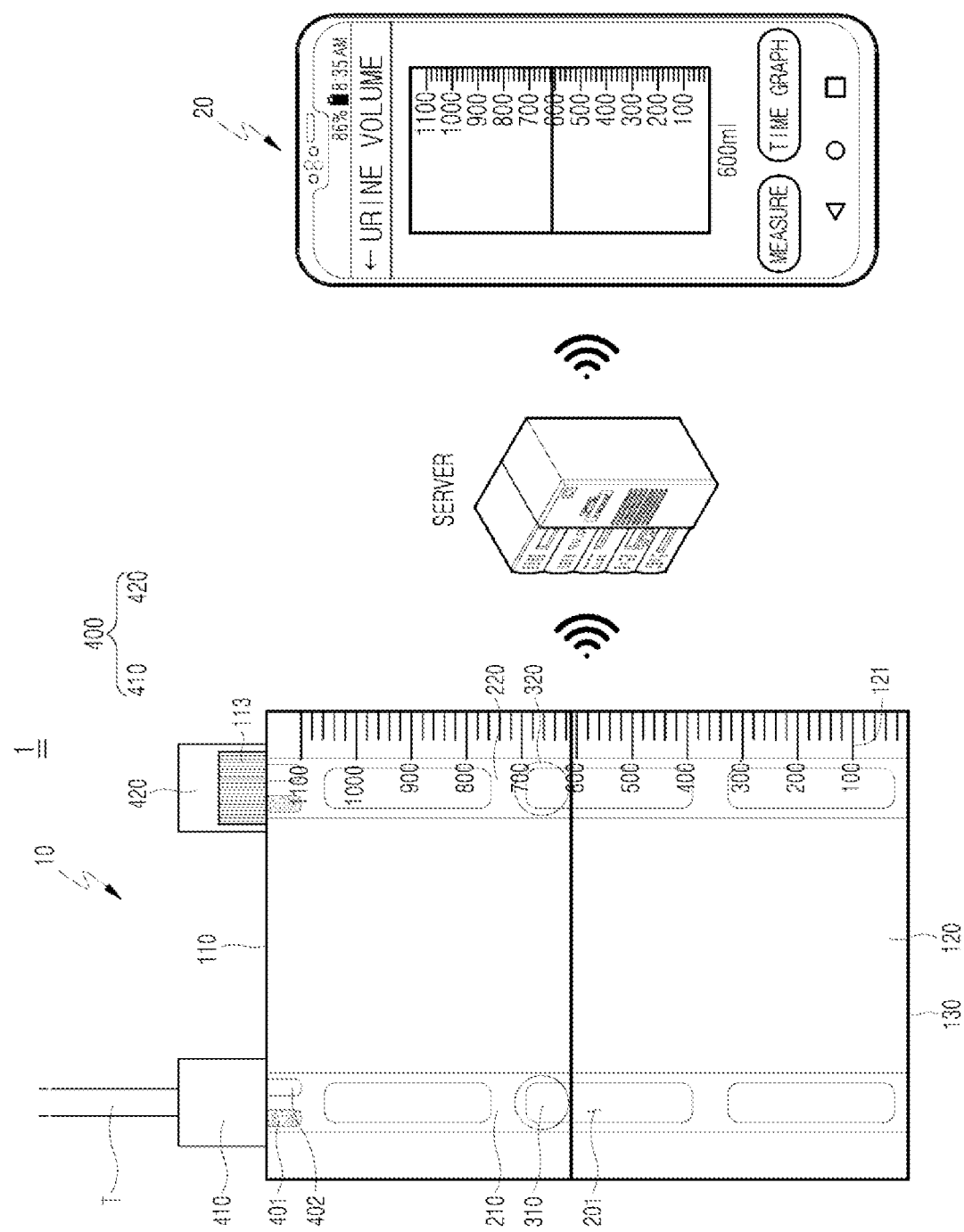
FIG. 5 is a side view illustrating a state in which a system for automatically measuring urine volume according to an embodiment of the present disclosure is being used.
Figure 6:
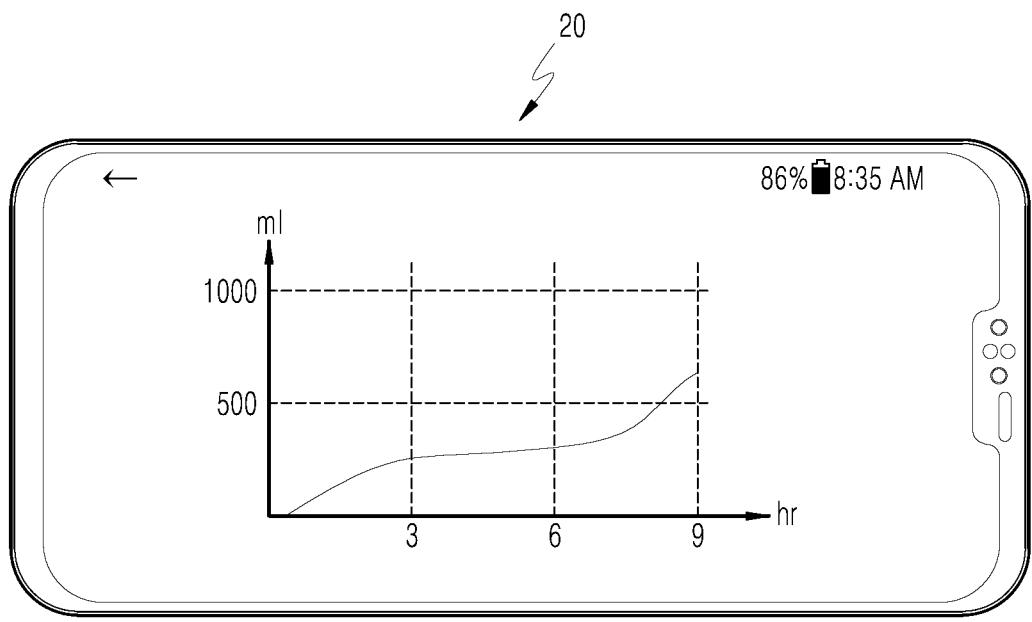
FIG. 6 is a view illustrating a state in which an output device of FIG. 5 is being used.
Figure 7:
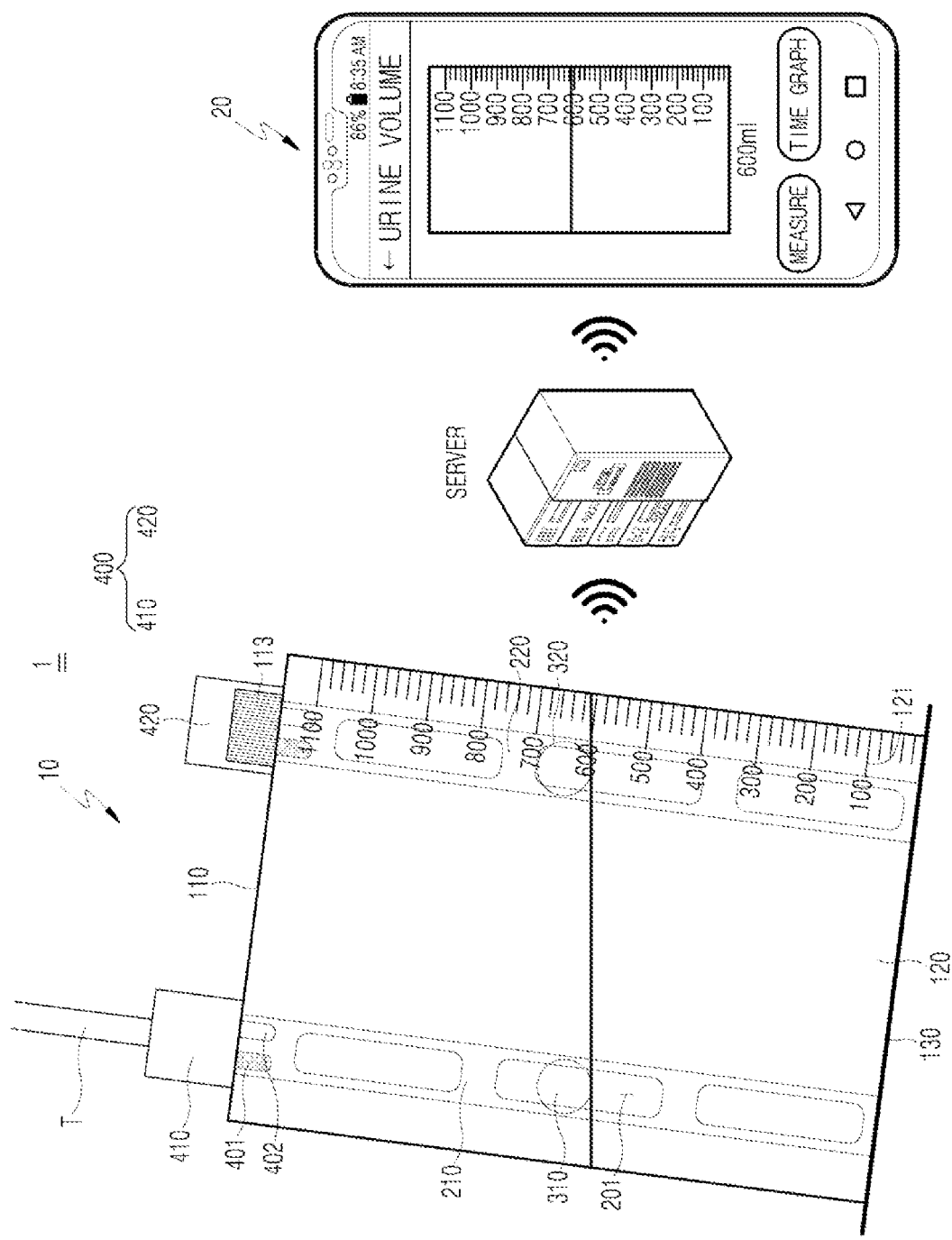
FIG. 7 is a side view illustrating a state in which the system for automatically measuring urine volume of FIG. 5 is being used.

FIG. 5 is a side view illustrating a state in which a system for automatically measuring urine volume 1 according to an embodiment of the present disclosure is being used. FIG. 6 is a view illustrating a state in which an output device 20 of FIG. 5 is being used. FIG. 7 is a side view illustrating a state in which the system for automatically measuring urine volume 1 of FIG. 5 is being used.

FIG. 8 is a perspective view of an apparatus for automatically measuring urine volume 10' according to another embodiment of the present disclosure. FIG. 9 is a perspective view of an apparatus for automatically measuring urine volume 10" according to yet another embodiment of the present disclosure.

Hereinafter, for easy understanding of the apparatus for automatically measuring urine volume 10 according to an embodiment of the present disclosure, up and down and left and right directions mentioned in the detailed description will be based on the attached drawings.

As illustrated in FIGS. 1 and 2, the apparatus for automatically measuring urine volume 10 according to an embodiment of the present disclosure may be configured to measure the correct volume of urine automatically and continuously, and may include a urine container 100, a hollow tube 200, a floating body 300, and a distance sensor 400.

As illustrated in FIGS. 1 and 2, the urine container 100 may be an element for storing urine of a patient, and may be made of a transparent material or a translucent material so that the state and color of the urine in the urine container 100 can easily be checked from the outside. The urine container 100 may be made of a plastic material, such as vinyl and polyethylene terephthalate (PET).

The urine container 100 may include a top surface 110, a side surface 120, and a bottom surface 130. The urine container 100 (when unfolded) may form a three-dimensional shape in which the top surface 110 and the bottom surface 130 are parallel to each other. For example, the urine container 100 may be formed in a rectangular parallelepiped shape, a regular cube shape, or a cylindrical shape. FIGS. 1 and 2 illustrate the urine container 100 formed in a rectangular parallelepiped shape. FIG. 8 illustrates the urine container 100 of a cylindrical shape.

As illustrated FIGS. 2 and 3, the side surface 120 of the urine container 100 may be folded and unfolded. A folding line 122 may be formed in the side surface 120 of the urine container 100. The folding line 122 may be a boundary line along which the side surface 120 of the urine container 100 is folded and unfolded.

The folding line 122 may be formed by a machine or an operator by folding the urine container 100 during manufacturing of the urine container 100. Alternatively, the folding line 122 may be formed by applying heat or force to the side surface 120 of the urine container 100 along the folding line 122 by using a press or the like during the manufacturing of the urine container 100.

Plastic is a material that is elastically deformed and plastic-deformed by heat or force. Accordingly, as illustrated in FIG. 3, when the urine container 100 is folded, a folded portion of the urine container 100 is partially plastic-deformed, and thus the folding line 122 may be permanently formed.

The manufacturing of the urine container 100 may be completed with the urine container 100 folded. Accordingly, the urine container 100 may be minimized in volume when the urine container 100 is delivered to or stored in a hospital.

As illustrated in FIG. 2, a hole 111, an outlet 112, an insertion hole 114, and a sticky portion 115 may be formed on the top surface 110 of the urine container 100.

As illustrated in FIGS. 1 and 2, the hole 111 may be an opening into which a urine catheter (T) is inserted. The urine catheter (T) may be connected to the urine container 100 through the hole 111. The urine catheter (T) may be a medical tube connected to a Foley catheter.

Foley catheter is a catheter that is located within the bladder by means of a spherule which can be inflated by air or liquid. Urine of a patient may flow into the urine container 100 through the Foley catheter and the urine catheter (T). Since the Foley catheter is a well-known technology, detailed description thereof will be omitted.

As illustrated in FIG. 2, the sticky portion 115 may be formed around the hole 111. The sticky portion 115 may be a sticky layer. The sticky portion 115 may be formed in the shape of a ring along a circumference of the hole 111. The sticky portion 115 may be formed of a double-sided adhesive tape of a ring shape. When the urine container 100 is not being used, the sticky layer of the sticky portion 115 may be protected by a protection sheet.

An adhering portion (TA) to be attached along the circumference of the hole 111 may be formed in the urine catheter (T). The adhering portion (TA) may be formed in the shape of a ring along a circumference of the urine catheter (T). A sticky layer may be formed on a lower surface of the adhering portion (TA). When the urine container 100 is not being used, the sticky layer of the adhering portion (TA) may be protected by a protection sheet.

As the urine catheter (T) is inserted into the hole 111, the lower surface of the adhering portion (TA) may be attached to the sticky portion 115. The lower surface of the adhering portion (TA) may form a relatively strong adhesion with the sticky portion 115. Accordingly, even when the urine container 100 is turned upside down by accident, the urine in the urine container 100 may be prevented from flowing out through the hole 111. In addition, evaporated urine may also be prevented from leaking through the hole 111.

As illustrated in FIGS. 1 and 2, the outlet 112 may be an opening through which the urine in the urine container 100 is discharged. The outlet 112 may be opened and closed by means of a lid 113. A male screw may be formed on an outer surface of the outlet 112. A female screw may be formed on an inner surface of the lid 113. The lid 113 may be rotated to be coupled to or decoupled from the outlet 112.

As illustrated in FIGS. 1 and 2, the insertion hole 114 may be an opening into which the hollow tube 200 is inserted. The insertion hole 114 may be two or more insertion holes 114. The distance sensor 400 may be two or more distance sensors 400. The number of the insertion holes 114 may be the same as the number of distance sensors 400.

FIGS. 1 and 2 illustrate the apparatus for automatically measuring urine volume 10 including two distance sensors 400. The insertion holes 114 may include a first insertion hole 114A and a second insertion hole 114B. The first insertion hole 114A and the second insertion hole 114B may be provided at symmetrical positions about a center of the top surface 110 of the urine container 100.

As illustrated in FIG. 2, when the urine container 100 has a rectangular parallelepiped shape, the first insertion hole 114A and the second insertion hole 114B may be provided in opposite corners of the top surface 110 of the urine container 100.

The sticky portion 115 may be formed along a circumference of each of the first insertion hole 114A and the second insertion hole 114B. The sticky portion 115 may be a sticky layer.

The sticky portion 115 may be formed in the shape of a ring along the circumference of each of the first insertion hole 114A and the second insertion hole 114B. The sticky portion 115 may be formed of a double-sided adhesive tape of a ring shape. When the urine container 100 is not being used, the sticky layers of the first insertion hole 114A and the second insertion hole 114B may be protected by a protection sheet.

Graduations 121 and numbers may be formed on the side surface 120 of the urine container 100. The graduations 121 and the numbers may indicate the volume of the urine in the urine container 100. A nurse may visually recognize the volume of the urine in the urine container 100 through the graduations 121 and the numbers.

The hollow tube 200 may be inserted into the insertion hole 114 in a gravity direction. The hollow tube 200 may be formed in a long straw shape extending in a vertical direction.

FIGS. 1 and 2 illustrate the apparatus for automatically measuring urine volume 10 including two distance sensors 400. The hollow tube 200 may be two or more hollow tubes 200, and the number of the hollow tubes 200 may be the same as the number of the distance sensors 400. The hollow tubes 200 may include a first hollow tube 210 and a second hollow tube 220. The first hollow tube 210 and the second hollow tube 220 may be formed in the same shape.

FIG. 8 illustrates the apparatus for automatically measuring urine volume 10' including three distance sensors 400. In the apparatus for automatically measuring urine volume 10', the hollow tubes 200 may include a first hollow tube 210, a second hollow tube 220, and a third hollow tube 230.

FIG. 9 illustrates the apparatus for automatically measuring urine volume 10" including four distance sensors 400. In the apparatus for automatically measuring urine volume 10", the hollow tubes 200 may include a first hollow tube 210, a second hollow tube 220, a third hollow tube 230, and a fourth hollow tube 240.

As illustrated in FIG. 2, the first hollow tube 210 may be inserted into the first insertion hole 114A in the gravity direction. The second hollow tube 220 may be inserted into the second insertion hole 114B in the gravity direction. Accordingly, the first hollow tube 210 and the second hollow tube 220 may be provided at symmetrical positions about the center of the top surface 110 of the urine container 100.

As illustrated in FIG. 2, one or more through holes 201 may be formed in each of the first hollow tube 210 and the second hollow tube 220. The through holes 201 may form a passage through which the urine in the urine container 100 flows into the hollow tube 200.

The through holes 201 may be formed in a shape extending in a vertical direction. Preferably, a plurality of through holes 201 may be formed between an upper end and a lower end of the hollow tube 200.

An adhering portion 202 may be formed in an upper portion of each of the first hollow tube 210 and the second hollow tube 220. The adhering portion 202 may be formed in the shape of a ring along a circumference of the upper portion of the hollow tube 200.

A sticky layer may be formed on an upper surface and a lower surface of the adhering portion 202. The lower surface of the adhering portion 202 may be attached to a circumference of the insertion hole 114. When the urine container 100 is not being used, the sticky layer in the adhering portion 202 may be protected by a protection sheet.

As the hollow tube 200 is inserted into the insertion hole 114, the lower surface of the adhering portion 202 may be attached to the sticky portion 115. The lower surface of the adhering portion 202 may form a relatively strong adhesion with the sticky portion 115.

Accordingly, the urine in the urine container 100 may be prevented from leaking between an outer surface of the hollow tube 200 and the insertion hole 114. In addition, evaporated urine may also be prevented from leaking between the outer surface of the hollow tube 200 and the insertion hole 114.

As illustrated in FIG. 2, an attachment portion 203 to be attached to an inner bottom surface of the urine container 100 may be formed in a lower portion of the hollow tube 200.

Lower ends of each of the first hollow tube 210 and the second hollow tube 220 may be blocked by a planar surface. The attachment portion 203 may be formed on an outer bottom surface of each of the first hollow tube 210 and the second hollow tube 220.

The attachment portion 203 may be a sticky layer. The attachment portion 203 may be formed of a double-sided adhesive tape. When the urine container 100 is not being used, the attachment portion 203 may be protected by a protection sheet.

As the hollow tube 200 is inserted into the insertion hole 114, the lower surface of the adhering portion 202 may be attached to the sticky portion 115. In addition, the attachment portion 203 at the lower end of the hollow tube 200 may be attached to the inner bottom surface of the urine container 100. Accordingly, movement of the hollow tube 200 with respect to the urine container 100 may be prevented.

As described in detail above, the urine container 100 may be minimized in volume when the urine container 100 is delivered to or stored in a hospital. When the apparatus for automatically measuring urine volume 10 is used, the urine container 100 may be unfolded such that the urine container 100 has a three-dimensional shape in which the top surface 110 and the bottom surface 130 are parallel to each other.

While the urine container 100 is being unfolded, the urine container 100 may be elastically deformed and plastic-deformed. Accordingly, a force to fold the urine container 100 back (i.e., elastic resilience) may be applied to the urine container 100.

The hollow tube 200 may have a rigidity against the force to fold the urine container 100 back. For example, the hollow tube 200 may be formed to have a thickness greater than a thickness of the urine container 100. Alternatively, the hollow tube 200 may be made of a material having a greater rigidity than a material of the urine container 100.

An unfolded state of the side surface 120 of the urine container 100 may be maintained by the rigidity of the first hollow tube 210 and the second hollow tube 220. In addition, a state in which the top surface 110 and the bottom surface 130 of the urine container 100 are parallel to each other may be maintained by the rigidity of the first hollow tube 210 and the second hollow tube 220.

Accordingly, the rigidity of the hollow tubes 200 may enable an inner space of the urine container 100 to maintain a constant volume. Consequently, the graduations 121 and the numbers on the side surface 120 of the urine container 100 may accurately show the volume of the urine in the urine container 100.

As illustrated in FIG. 2, a floating body 300 may be inserted into the hollow tube 200 so as to move up and down. The floating body 300 may have buoyancy to float on the urine. The floating body 300 may be made of a material such as Styrofoam or plastic, which has a specific gravity smaller than that of urine.

FIGS. 1 and 2 illustrate the apparatus for automatically measuring urine volume 10 including two distance sensors 400. The floating body 300 may be two or more floating bodies 300, and the number of the floating bodies 300 may be the same as the number of the distance sensors 400. The floating bodies 300 may include a first floating body 310 and a second floating body 320. The first floating body 310 may be inserted into the first hollow tube 210 so as to move up and down. The second floating body 320 may be inserted into the second hollow tube 220 so as to move up and down.

FIG. 8 illustrates the apparatus for automatically measuring urine volume 10' including three distance sensors 400. In the apparatus for automatically measuring urine volume 10', the floating bodies 300 may include a first floating body 310, a second floating body 320, and a third floating body 330.

FIG. 9 illustrates the apparatus for automatically measuring urine volume 10" including four distance sensors 400. In the apparatus for automatically measuring urine volume 10", the floating bodies 300 may include a first floating body 310, a second floating body 320, a third floating body 330, and a fourth floating body 340.

The floating bodies 300 may be formed in various shapes. That is, the floating bodies 300 may be formed in a sphere shape, a disk shape, or a polyhedron shape. FIG. 2 illustrates the floating bodies 300 formed in a sphere shape.

As illustrated in FIG. 4, when the urine container 100 is empty, the first floating body 310 and the second floating body 320 may be at the lowermost portion within the hollow tubes 200.

As illustrated in FIG. 5, when urine has flowed into the urine container 100, the first floating body 310 and the second floating body 320 may float on the urine within the hollow tubes 200.

As illustrated in FIG. 2, the distance sensors 400 may be provided at upper portions of the hollow tubes 200 so as to measure a distance to the floating bodies 300.

The distance sensors 400 may be ultrasonic sensors. An ultrasonic sensor is a sensor configured to measure the distance to the floating body 300 by using an ultrasonic wave method.

The ultrasonic wave method is a method to determine a distance to an object by transmitting an ultrasonic wave with sharp directivity to the object and measuring the time taken until a reflected wave is received from the object. As a receiving sensor 402, a piezoelectric element may be used. Since the distance sensor 400 is a well-known technology, detailed description thereof will be omitted.

As illustrated in detail above, the adhering portion 202 may be formed in the upper portion of the hollow tube 200. The adhering portion 202 may be formed in the shape of a ring along a circumference of the upper portion of the hollow tube 200. A sticky layer may be formed on the upper surface and the lower surface of the adhering portion 202. When the urine container 100 is not being used, the sticky layer in the adhering portion 202 may be protected by a protection sheet.

An ultrasonic wave oscillating part 401 and the receiving sensor 402 may be provided in a lower portion of the distance sensor 400. Also, an adhering surface 403 may be formed on a bottom surface of the distance sensor 400 in the form of a ring. The adhering surface 403 may be formed around a lower circumference of the distance sensor 400 to surround the ultrasonic wave oscillating part 401 and the receiving sensor 402.

As the ultrasonic wave oscillating part 401 and the receiving sensor 402 are inserted into an upper opening of the hollow tube 200, the adhering surface 403 may be mounted on the upper surface of the adhering portion 202.

The sticky layer on the upper surface of the adhering portion 202 may form a relatively strong adhesion with the adhering surface 403.

That is, the upper surface of the adhering portion 202 may be attached along the lower circumference of the distance sensor 400. Accordingly, even when the urine container 100 is turned upside down by accident, the urine in the urine container 100 may be prevented from leaking through the hollow tubes 200. In addition, evaporated urine may also be prevented from leaking through the hollow tubes 200.

FIGS. 1 and 2 illustrate the apparatus for automatically measuring urine volume 10 including two distance sensors 400. As illustrated in FIG. 2, the distance sensors 400 may include the first distance sensor 410 and the second distance sensor 420.

The ultrasonic wave oscillating part 401 and the receiving sensor 402 of the first distance sensor 410 may be inserted into an upper opening of the first hollow tube 210. Accordingly, the first distance sensor 410 may measure a distance to the first floating body 310.

The ultrasonic wave oscillating part 401 and the receiving sensor 402 of the second distance sensor 420 may be inserted into an upper opening of the second hollow tube 220. Accordingly, the second distance sensor 420 may measure a distance to the second floating body 320.

As illustrated in FIG. 8, in the urine container 100 of a cylindrical shape, the distance sensors 400 may be disposed to form equal angles with each other about the center of the top surface 110 of the urine container 100. For example, when three distance sensors 400 are provided, the distance sensors 400 may be disposed to form a 120-degree angle with each other about the center of the top surface 110 of the urine container 100.

FIG. 9 illustrates the apparatus for automatically measuring urine volume 10" including four distance sensors 400. When four distance sensors 400 are provided, the distance sensors 400 may be disposed to form a 90-degree angle with each other about the center of the top surface 110 of the urine container 100. In the urine container 100 of a rectangular parallelepiped shape, the distance sensors 400 may be disposed at each corner on the top surface 110 of the urine container 100.

As illustrated in FIG. 5, the system for automatically measuring urine volume 1 according to an embodiment of the present disclosure may include the apparatus for automatically measuring urine volume 10 described in detailed above and an output device 20.

The output device 20 may be a device configured to receive measurements of the distance sensors 400 and to output the volume of urine. A patient monitoring program or an application for medical staff may be installed in the output device 20. The output device 20 may include a PC, a mobile tablet, and a smart phone. The PC and the mobile tablet may be provided in a nurse office or the like.

The measurements of the distance sensors 400 may be automatically transmitted to a cloud server or a private server and then stored therein. Thereafter, the measurements may be wirelessly transmitted (i.e., downloaded) to the PC, the mobile tablet, and the smart phone. The apparatus for automatically measuring urine volume 10 may wirelessly transmit the measurements of the distance sensors 400, through a local area network such as WiFi, to the cloud server or the private server.

A cloud service is a service that enables users to store various data not in a PC or a smart phone but in an external cloud server, and to download the stored data. Accordingly, medical staff may store various medical information including monitoring information of patients in a cloud server, and may conveniently manage and use the medical information through a smart phone or a PC.

The PC may store therein the patient monitoring program configured to calculate the volume of urine in the urine container 100 through the measurements of the distance sensors 400 and output a result of the calculation to a screen.

The mobile tablet and the smart phone may store therein the application for medical staff configured to calculate the volume of urine in the urine container 100 through the measurements of the distance sensors 400 and output a result of the calculation to a screen. FIG. 5 illustrates, on the right side, a smart phone running the application.

As illustrated in FIG. 5, the application may output, to the screen, the volume of the urine in the urine container 100 in real time. As illustrated in FIG. 6, the application may output, to the screen, a graph with time on the x-axis and the volume of the urine in the urine container 100 on the y-axis.

As described in detail above, the hollow tubes 200 may be provided at symmetrical positions about the center of the top surface 110 of the urine container 100. Accordingly, the first distance sensor 410 and the second distance sensor 420 may be provided at symmetrical positions about the center of the top surface 110 of the urine container 100.

That is, the first distance sensor 410 and the second distance sensor 420 may measure, respectively, the distances to the first floating body 310 and the second floating body 320, at symmetrical positions about the center of the top surface 110 of the urine container 100.

As illustrated in FIG. 7, when the urine container 100 is tilted, a distance from the center of the top surface 110 of the urine container 100 to the raised first distance sensor 410 may be the same as a distance from the center of the top surface 110 of the urine container 100 to the lowered second distance sensor 420.

Accordingly, even when the urine container 100 is tilted, an average of a measurement of the first distance sensor 410 and a measurement of the second distance sensor 420 may correspond to the volume of the urine in the urine container 100.

The output device 20 may output the volume of urine by calculating the average of the measurements of the first distance sensor 410 and the second distance sensor 420. Accordingly, in the system for automatically measuring urine volume 1, even when the urine container 100 is tilted, the correct volume of urine may be outputted to the output device 20.

According to the present disclosure, the apparatus for automatically measuring urine volume and the system for automatically measuring urine volume are characterized in that as the volume of the urine in the urine container is measured by using the measurements of the distance sensors, and the output device outputs the volume of urine, the correct volume of urine may be automatically and continuously measured regardless of the tilt of the urine container, the weight of the Foley catheter, and the presence of a nurse who directly checks the volume of urine, so as to accurately recognize a change in the volume of urine and anticipate a probable emergency situation based on the change in the volume of urine.

While specific exemplary embodiments of the present disclosure are described and illustrated above, it would be obvious to those skilled in the art that various modifications and variations can be made thereto within the spirit and scope of the present disclosure. Accordingly, such modifications or variations are not to be regarded as a departure from the spirit or scope of the present disclosure, and it is

DESCRIPTION OF SYMBOLS

1: SYSTEM FOR AUTOMATICALLY MEASURING URINE VOLUME
10, 10', 10": APPARATUS FOR AUTOMATICALLY MEASURING URINE VOLUME
20: OUTPUT DEVICE
100: URINE CONTAINER
110: TOP SURFACE
111: HOLE
112: OUTLET
113: LID
114: INSERTION HOLE
114A: FIRST INSERTION HOLE
114B: SECOND INSERTION HOLE
115: STICKY PORTION
120: SIDE SURFACE
121: GRADUATION
122: FOLDING LINE
130: BOTTOM SURFACE PART
T: URINE CATHETER
TA: ADHERING PORTION
200: HOLLOW TUBE
210: FIRST HOLLOW TUBE
220: SECOND HOLLOW TUBE
201: THROUGH HOLE
202: ADHERING PORTION
203: ATTACHMENT PORTION
300: FLOATING BODY
310: FIRST FLOATING BODY
320: SECOND FLOATING BODY
400: DISTANCE SENSOR
410: FIRST DISTANCE SENSOR
420: SECOND DISTANCE SENSOR
401: ULTRASONIC WAVE OSCILLATING
402: RECEIVING SENSOR
403: ADHERING SURFACE

What is claimed is:

1. An apparatus for automatically measuring urine volume, the apparatus comprising:
a urine container to which a urine catheter is connected, wherein an insertion hole is formed in an upper portion of the urine container;
a hollow tube inserted into the insertion hole in a gravity direction;
a floating body inserted into the hollow tube so as to move up and down and having buoyancy to float on the urine; and
a distance sensor provided at an upper portion of the hollow tube so as to measure a distance to the floating body,
wherein the volume of the urine in the urine container is configured to be measured by using a measurement of the distance sensor,
wherein an adhering portion is configured to be attached around the insertion hole by a sticky layer formed in the upper portion of the hollow tube,
wherein an attachment portion is configured to be attached to an inner bottom surface of the urine container by a sticky layer formed in a lower portion of the hollow tube, and
wherein a side surface of the urine container is configured to be folded and unfolded, the side surface of the urine container is maintained in an unfolded state by a rigidity of the hollow tube.

2. The apparatus for automatically measuring urine volume of claim 1, wherein one or more through holes are formed in the hollow tube such that urine can flow into the hollow tube.

3. The apparatus for automatically measuring urine volume of claim 1, wherein
an upper surface of the adhering portion is attached around a bottom edge of the distance sensor such that the urine container is sealed.

4. The apparatus for automatically measuring urine volume of claim 1, wherein
the urine container is formed in a three-dimensional shape in which a top surface and a bottom surface of the urine container are parallel to each other,
the hollow tube is provided as two or more hollow tubes comprising a first hollow tube and a second hollow tube, which are disposed at symmetrical positions about a center of the top surface of the urine container, and
the top surface and the bottom surface of the urine container are maintained to be parallel to each other by a rigidity of the first hollow tube and the second hollow tube.

5. A system for automatically measuring urine volume, the system comprising:
the apparatus for automatically measuring urine volume of claim 1; and
an output device configured to receive a measurement of the distance sensor from a server and output the volume of urine,
wherein the measurement of the distance sensor is transmitted to the server.

6. The system for automatically measuring urine volume of claim 5,
wherein the urine container is formed in a three-dimensional shape in which a top surface and a bottom surface of the urine container are parallel to each other,
wherein the distance sensor is provided as two or more distance sensors comprising a first distance sensor and a second distance sensor,
wherein the first distance sensor and the second distance sensor are provided at symmetrical positions about a center of the top surface of the urine container, such that even when the urine container is tilted, an average of a measurement of the first distance sensor and a measurement of the second distance sensor corresponds to the volume of urine, and
wherein the output device calculates the average of the measurements of the first distance sensor and the second distance sensor and output the volume of urine.

* * * * *